(12) United States Patent
An et al.

(10) Patent No.: US 9,829,482 B2
(45) Date of Patent: Nov. 28, 2017

(54) MOTILITY-CONTRAST IMAGING FOR OOCYTE AND EMBRYO VIABILITY ASSESSMENT

(71) Applicant: Purdue Research Foundation, West Lafayette, IN (US)

(72) Inventors: Ran An, West Lafayette, IN (US); David D. Nolte, Lafayette, IN (US); Zoltan Machaty, West Lafayette, IN (US); John J. Turek, West Lafayette, IN (US)

(73) Assignee: PURDUE RESEARCH FOUNDATION, West Lafayette, IN (US)

( * ) Notice: Subject to any disclaimer, the term of this patent is extended or adjusted under 35 U.S.C. 154(b) by 266 days.

(21) Appl. No.: 14/026,799

(22) Filed: Sep. 13, 2013

(65) Prior Publication Data

US 2015/0079621 A1 Mar. 19, 2015
US 2017/0102376 A9 Apr. 13, 2017

Related U.S. Application Data

(60) Provisional application No. 61/700,378, filed on Sep. 13, 2012.

(51) Int. Cl.
*G01N 33/50* (2006.01)
*G01N 15/14* (2006.01)

(52) U.S. Cl.
CPC ..... *G01N 33/5091* (2013.01); *G01N 15/1475* (2013.01)

(58) Field of Classification Search
None
See application file for complete search history.

(56) References Cited

U.S. PATENT DOCUMENTS 8,337,387 B2 * 12/2012 Wong et al. .................. 600/33
8,886,295 B2 * 11/2014 Nolte et al. .................. 600/476

OTHER PUBLICATIONS

Montag et al. "Oocyte assessment and embryo viability prediction: birefringence imaging". Reproductive BioMedecine Online. May 2008, vol. 17, No. 4, pp. 454-460.*
Jeong "Holographic optical coherence imaging of living tissues". Dissertation, 2007.*
Ebner, T., et al, "Selection based on morphological assessment of oocytes and embryos at different stages of preimplantation development: a review," Human Reproduction Update, vol. 9, May-Jun. 2003, pp. 251-262.
Sato, C., et al, "Assessment of human oocyte developmental competence by cumulus cell morphology and circulating hormone profile," Reproductive Biomedicine Online, vol. 14, pp. 49-56, Jan. 2007.
Salvador, M., et al., "Depth-resolved holographic optical coherence imaging using a high-sensitivity photorefractive polymer device," Applied Physics Letters, vol. 93, Dec. 8, 2008.
Jeong, K., et al, "Fourier-Domain Digital Holographic Optical Coherence Imaging of Living Tissue," Appl. Opt., vol. 46, pp. 4999-5008, 2007.
Jeong, K., et al, "Fourier-Domain Holographic Optical Coherence Imaging of Tumor Spheroids and Mouse Eye," Appl. Opt., vol. 44, pp. 1798-1805, Apr. 1, 2005.
Nolte, D.D., et al, "Holographic Motility Contrast Imaging of Live Tissues," Chap. in Biomedical Optical Phase Microscopy and Nanoscopy, N.T. Shaked, Z. Salevskey, and L. Sattterwhite, Eds., ed: Elsevier, 2012.
Nolte, D.D., et al, "Dynamic Light Scattering and Motility Contrast Imaging in Living Tissue," Chap. in Biomedical Applications of Light Scattering, A. Wax and V. Backman, Eds., ed: McGraw Hill, 2010.
Jeong, K., et al, Phase-Sensitive Motility Contrast Imaging of Tumor Response to Drugs, 2010.
Nolte, D.D., et al, "Tissue Dynamics Spectroscopy for Phenotypic Profiling of Drug Effects in Three-Dimensional Culture," Biomed. Opt. Express, vol. 3, pp. 2825-2841, 2012.
Nolte, D.D., et al, "Holographic Tissue Dynamics Spectroscopy," Journal of Biomedical Optics, vol. 16, pp. 087004-087013, Aug. 2011.
Nolte, D.D., "Tissue Dynamics Spectroscopy for Three-Dimensional Tissue-Based Drug Screening," Jala, vol. 16, pp. 431-442, Dec. 2011.
Jeong, K., et al, "Multiple-Scattering Speckle in Holographic Optical Coherence Imaging," Applied Physics B—Lasers and Optics, col. 95, pp. 617-625, Jun. 2009.
Yamaguchi, I. and Zhang, T., "Phase-Shifting Digital Holography," Optics Letters, vol. 22, pp. 1268-1270, Aug. 15, 1997.
Cuche, E., et al "Digital Holography for Quantitative Phase—Contrast Imaging," Optics Letters, vol. 24, pp. 291-293, Mar. 1, 1999.
Dubois, F., et al, "Improved Three-Dimensional Imaging With a Digital Holography Microscope With a Source of Partial Spatial Coherence," Applied Optics, vol. 38, pp. 7085-7094, Dec. 1, 1999.
Huang, T.S., "Digital Holography," Proceedings of the Institute of Electrical and Electronics Engineers, vol. 59, pp. 1335-1351, 1971.
Posescu, G. and Dogariu, A., "Scattering of Low Coherence Radiation and Applications," European Physical Journal—Applied Physics, vol. 32, pp. 73-93, Nov. 2005.
Chalut, K.J., et al, "Label-Free, High-Throughput Measurements of Dynamic Changes in Cell Nuclei Using Angle-Resolved Low Coherence Interferometry," Biophysical Journal, vol. 94, pp. 4948-4956, Jun. 15, 2008.

* cited by examiner

*Primary Examiner* — Vera Afremova
(74) *Attorney, Agent, or Firm* — Bose McKinney & Evans LLP

(57) ABSTRACT

A method and system is provided for evaluating viability of oocytes and embryos comprising imaging an oocyte or embryo using motility contrast imaging; generating temporal contrast and spatial contrast data for the cells; generating a cell viability value as a function of the temporal and spatial contrast data; and comparing the cell viability value to a predetermined value indicative of a cell suitable for use in an in vitro fertilization program.

24 Claims, 11 Drawing Sheets

MOTILITY-CONTRAST IMAGING FOR OOCYTE AND EMBRYO VIABILITY ASSESSMENT

CROSS-REFERENCE TO RELATED APPLICATION

The present application is a utility conversion of and claims priority to provisional application No. 61/700,378, filed on Sep. 13, 2012, the entire disclosure of which is incorporated herein by reference.

STATEMENT OF GOVERNMENT SUPPORT

The invention was made with government support under Grant CBET-0756005 awarded by the National Science Foundation. The U.S. Government has certain rights in the invention.

FIELD

The present disclosure relates generally to the assessment of oocytes and embryos for use in in vitro fertilization programs, and particularly to systems and methods for using motility contrast imaging techniques to assess cell viability.

BACKGROUND

Since the first successful pregnancy following in vitro fertilization (IVF) was achieved in 1978, improvement in the techniques of assisted reproductive technologies has led to an increased success rate in the field of treating human infertility. Success in IVF programs is typically dependent upon the selection of the best embryo chosen for transfer to the uterus. Because of uncertainty in the functional viability of oocytes or early embryos, clinicians frequently transferred many embryos simultaneously. While improving the rate of pregnancy after IVF, this approach has also led to an increase in the rates of multiple pregnancies. The dangers of multiple pregnancies for both the mother and the neonates are well documented, and twin birth is now considered an undesirable outcome of IVF.

In the early years of IVF, embryo viability was considered to be a function of developmental progression during the pre-implantation phase. Over the last decade, the focus has been on the evaluation of certain morphological criteria of the oocyte or embryonic cells. The current approach to determining oocyte/embryo viability involves an indirect and subjective scoring system based on morphologically observable traits under a microscope [1, 2]. Scoring oocytes/embryos requires a highly skilled technician that takes the average clinical embryologist at least three months to learn. Although this approach has had some predictive value, it has been frequently criticized as imperfect and unreliable, generally thought to yield only a 23% average success rate. In many cases a selected oocyte or embryo may have normal morphology, as observed by the embryologist, but possess undetected alterations in their biochemistry that affect viability. For instance, oocytes invested with cumulus granulosa cells, called cumulus-oocyte complexes (COC), are not readily visible under a microscope because they are obscured underneath the cumulus cells, making viability grading difficult. The question of viability becomes more pronounced for cryopreserved cells once thawed. Furthermore, after fertilization, the combined sperm and egg form the zygote (a single cell embryo) in which dramatic functional changes take place that are not readily visible under conventional microscopes. One such current microscope relies on Hoffman modulation contrast that is used to visualize oocytes and zygotes.

However, currently there are no imaging modalities that capture the functional viability of oocytes, or early embryos prior to implantation inside the uterus.

SUMMARY

The present disclosure contemplates a system and a method is provided for evaluating intracellular activity as a measure of oocyte/embryo viability. In one aspect, the intracellular activity is measured using motility contrast imaging. In certain examples described herein, motility contrast imaging (MCI) is used prior to and following stimulated maturation of a live oocyte in vitro to provide a new type of functional biomarker for candidate oocyte evaluation. In another aspect, the intracellular activity is measured using biodynamic spectroscopy. In certain examples described herein, biodynamic spectroscopy is used during embryo development through first cleavage. The systems and methods described herein can be used to evaluate viability of reproductive cells, including oocytes and embryos.

In one embodiment, the present invention provides a method for evaluating viability of oocytes and embryos comprising imaging using motility contrast imaging; generating temporal contrast and spatial contrast data for the oocyte or embryo; generating a cell viability value as a function of the temporal and spatial contrast data; and comparing the cell viability value to a predetermined value indicative of cells suitable for use in an in vitro fertilization program.

Another embodiment provides a method for evaluating viability of oocytes and embryos that includes reversibly immobilizing reproductive cells, detecting intracellular motion within the immobilized cells, generating a measure of dynamic activity of the cells, and comparing the measure of dynamic activity to a threshold indicative of cell viability. In such a method, the step of generating a measure of dynamic activity may include determining the temporal variation of the frequency content of speckle imaging of the cell, and deriving a viability figure in relation to the temporal and spatial variation of the frequency content; and the step of comparing the measure of dynamic activity to a threshold indicative of cell viability includes comparing the viability figure to the threshold.

DETAILED DESCRIPTION

Figure 1:
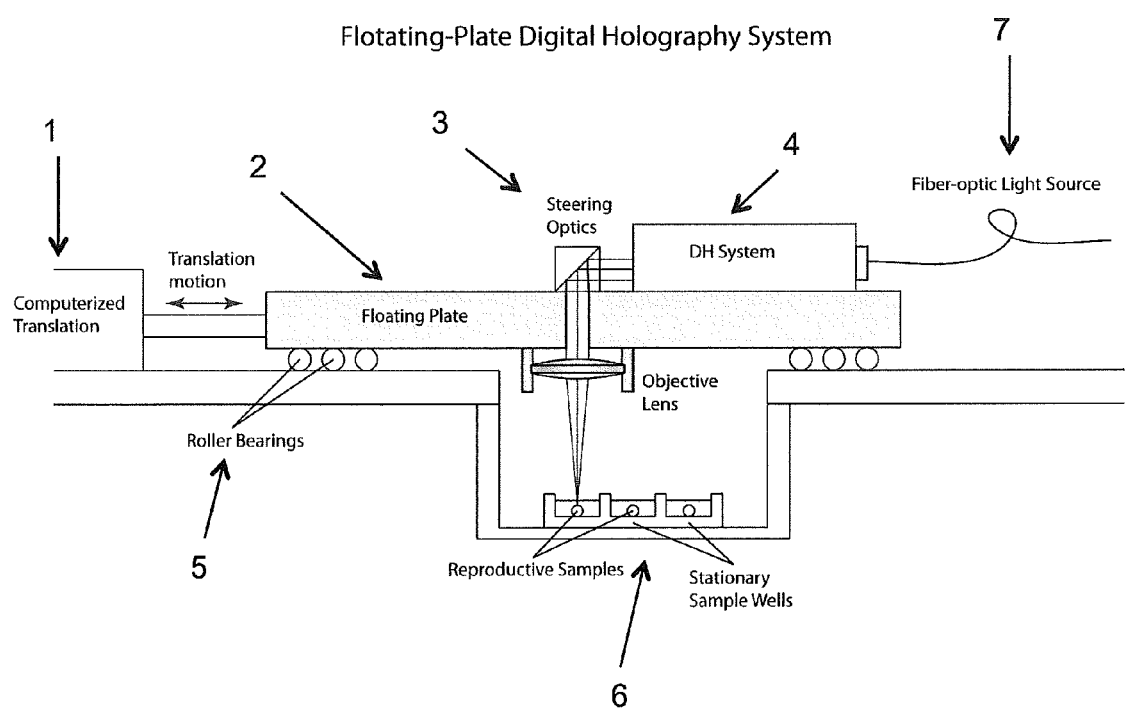
FIG. 1 is a diagram of a floating-plate digital holography system disclosed herein that protects weakly immobilized oocytes and embryos from stresses induced by motion of the sample wells.

For the purposes of promoting an understanding of the principles of the invention, reference will now be made to the embodiments illustrated in the drawings and described in the following written specification. It is understood that no limitation to the scope of the invention is thereby intended. It is further understood that the present invention includes any alterations and modifications to the illustrated embodiments and includes further applications of the principles of the invention as would normally occur to one skilled in the art to which this invention pertains.

Biodynamic Imaging

Biodynamic imaging (BDI) is the general term used to denote a range of related approaches that extract motion information from inside living tissue. BDI includes optical coherence imaging (OCI) [3-5], motility contrast imaging (MCI) [6-8], and tissue dynamics spectroscopy (TDS) [9-11]. All of these approaches have been applied to macroscopic tissues containing up to a million cells and down to about 50,000 cells, but never on a single cell like an oocyte because the techniques require high light scattering to provide detectable signal.

One of these approaches, named motility contrast imaging (MCI), uses subcellular motion as a form of endogenous image contrast [12]. MCI can be well suited for the evaluation of oocyte and embryo quality because MCI non-invasively captures the functional dynamics of the cells and tissues without exogenous dyes. Motility Contrast Imaging is based on Optical Coherence Imaging (OCI) which uses low-coherence Fourier-domain digital holography [4, 5]. OCI collects and distinguishes back scattered light deep from living tissue up to about 1 mm in thickness [13].

A protocol for oocyte/embryo immobilization is an important element of the disclosed system and method that allows oocytes and embryos that are graded as "good" by MCI to be ultimately implanted in utero. All previous applications of MCI to living tissue have used irreversible immobilization of the sample. Because MCI is motion-sensitive, the sample must be immobilized in the sample well or Petri dish so that only intracellular motions are detected, and not the gross motion of the sample.

In one approach for oocyte and embryo immobilization, a 2% solution of gelatin suitable for cell culture is diluted 1:1 with phosphate buffered oocyte culture medium and 300 μl of the solution added to each well of an 8-well Lab-Tek 1×3 glass slide. The culture slide is placed covered on a warming tray and held at 37-39° C. for 3-4 hours. After incubation the culture slide cover is removed and the medium is discarded. The culture slide is placed back on the warming tray without the cover inside a laminar flow hood with an ultraviolet light. The slide is ready for use after 1-2 hours of drying. Oocytes in phosphate buffered culture medium are placed in the 8 well plates and incubated in a $CO_2$ incubator at an appropriate physiological temperature (37° C. for humans, 39° C. for pigs). Oocytes adhere gently to the underlying surface after several hours in the incubator and are then ready for fertilization. Oocytes selected for fertilization based upon MCI viability scores are maintained in the phosphate buffered medium until after fertilization and the medium may be replaced with a HEPES buffered medium for observation of the fertilized oocyte outside of the incubator on a warming stage of the MCI instrument. The fertilized oocytes with the best MCI viability scores are removed for implantation by gentle pipetting the culture medium up and down several times. The fertilized oocytes with the best MCI viability metrics are now ready for implantation.

An important aspect of the protocol of the present disclosure is the tunability of the immobilization strength. By adjusting the percent gelatin and percent dilution by medium, the "stickiness" of the underlying layer can be adjusted to release the living samples more easily.

An embodiment of the present system and method strikes a compromise between immobilization strength and perturbation of the sample by system movements. Currently, the immobilized samples in the stage are moved and the optics remain stationary. The moving stage causes inertial forces on the samples that can make them move. In this embodiment, the weakest immobilization that is compatible with a stationary stage is used, and the detection optics is moved rather than the sample stage. The use of the weakest immobilization ensures that the reproductive samples are removed after MCI assessment without any unnecessary stress.

The implementation of moving optics, instead of a moving stage, requires special attention because of the use of digital holography. Digital holography is highly sensitive to vibrations and is performed on stationary plates or tables. To implement the moving optics under digital holography, one embodiment contemplates "floating plate" digital holography upon which the fixed-steering optics 3 and digital holography optics 4 reside, as shown in the exemplary system depicted in FIG. 1. A "floating plate" 2 is mounted on low-friction sliders 5 that are moved with computer-controlled actuators 1. The light source can be from a fiber optic feed 7 that is free to move as the floating plate moves. The floating plate digital holography disclosed herein solves the problem of keeping the sample stationary, while scanning from well-to-well, and while ultra-stable holography is performed.

Figure 2:
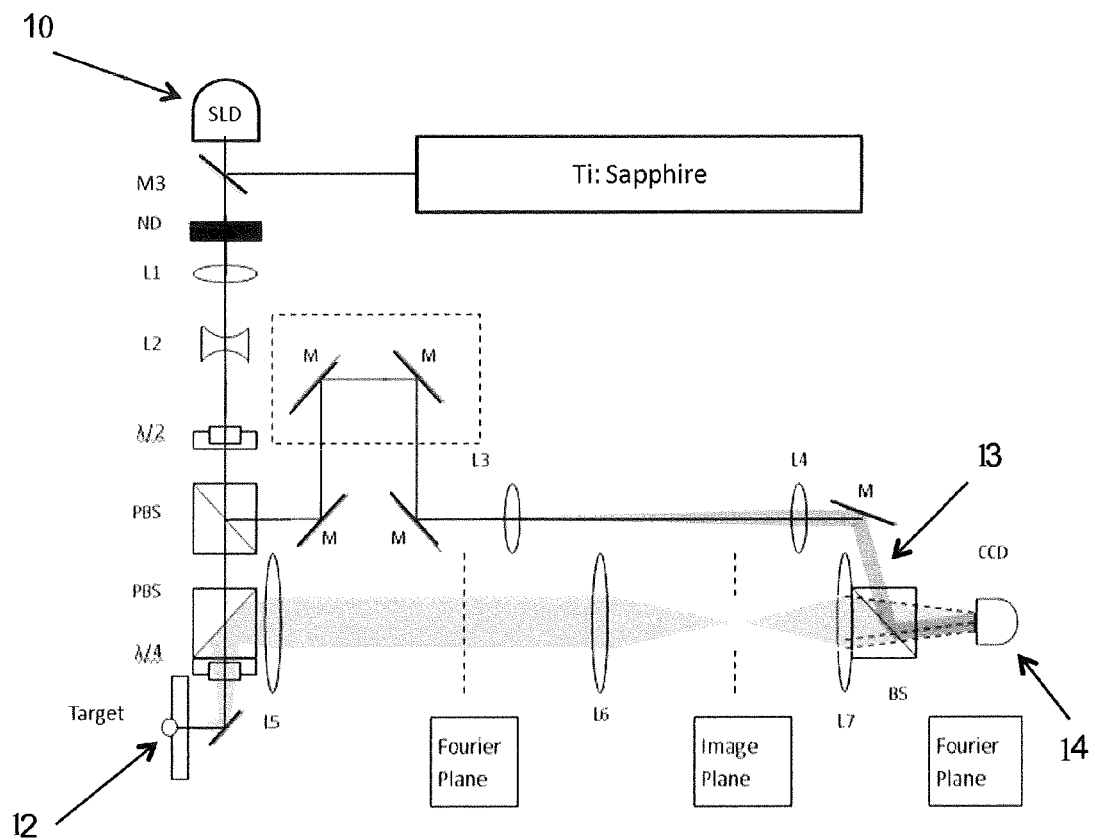
FIG. 2 is a diagram of the motility contrast imaging system for determining oocyte and embryo viability.

The optical elements of the holographic system of FIG. 1 is shown in FIG. 2. In one experimental setup the system is based on a Mach-Zehnder interferometer. Short coherence light is generated by a superluminescent diode 10 having a center wavelength of approximately 840 nm and a bandwidth of 50 nm in a specific embodiment. The light is collimated by lenses L1, L2 and then divided into two paths by a polarizing beam splitter to produce an object beam with vertical polarization and a reference beam with horizontal polarization. The object beam strikes the sample 12 which is in an environmentally controlled chamber with growth medium. Wave plates and polarizing beam splitters control beam intensity and ensure that most of the incoming light is directed into the object path and that most of the back scattered signal is directed to an EMC2 CCD camera 14. The CCD camera can be a 12-bit CCD camera with one megapixel resolution and an exposure time of 10 msec. Lens L5 performs an optical Fourier transform to the image plane, followed by a 4-f system L6, L7 that transfers the Fourier domain to a CCD screen with a ⅓× magnitude. A delay stage, including lens L4, is provided in the reference path to path-match the interfering images and to perform volumetric scanning of the living tissue. The interference fringes between the backscattered object beam and the reference beam 13 are recorded by the CCD and passed to a computer which is configured to construct a digital hologram at successive times. Images at successive depths in the target cell may be stacked to create volumetric images. Further details of a suitable system and method for performing motility contrast imaging are found in co-pending application Ser. No. 12/874,855, filed on Sep. 2, 2010, assigned to the assignee of the present invention and published as US2010-0331672-A1, the disclosure of which is incorporated herein by reference.

Oocytes and Embryos

To prepare for in vitro fertilization and early embryonic development, oocytes must be matured through the reinitiation and completion of the first meiotic division from the germinal vesicle stage to metaphase II. Oocytes are encased (invested) in a multilayer shell of cumulus granulosa cells that produce compounds that are essential for normal oocyte development. Cumulus cells transmit maturation signals to the oocyte. Part of the maturation process is the expansion of the cumulus cells, meaning an increase in the thickness of the investment, in response to exposure to luteinizing hormone (LH) and follicle stimulating hormone (FSH). Cumulus cells are capable of undergoing expansion in response to FSH in vitro in which accumulation of hyaluronan (HA), an extracellular matrix component of cumulus cells, brings about expansion of cumulus-oocyte complexes (COCs).

In one experiment, cumulus-invested pig oocytes were harvested immature and were matured in vitro. Ovaries from slaughtered gilts were transported in a warm environment (28-33° C.) to the laboratory where they were washed in 0.9% NaCl containing 100000 IU/L penicillin and 100 mg/L streptomycin. Cumulus-oocyte complexes (COCs) were aspirated from 3-8 mm antral follicles using a 10 mL syringe and an 18-gauge needle. For in vitro maturation, cumulus-oocyte complexes were cultured in 500 μL, Medium 199 (Earle's salts, L-glutamine, 2.2 mg/L sodium bicarbonate) supplemented with 10% (v/v) fetal bovine serum, 0.5 mg/L follicle-stimulating hormone, 0.5 mg/L luteinizing hormone, 0.57 mM cysteine and 50 mg/L gentamicin sulfate under mineral oil, at 39° C. for 48 h in a 5% $CO_2$ atmosphere.

In accordance with the present invention, MCI was applied to two groups of COCs—47 immature and 48 in vitro matured COCs. When collecting data, pig oocytes were placed in an S-well chamber slide at 39° C. filled with growth medium. For each oocyte, 500 successive images were captured at 25 fps at an exposure time of 10 msec using the MCI system shown in FIG. 1.

$I_H(x',y')$ is the intensity captured by the CCD camera given by the expression:

$$I_H(x',y')=|\psi_R+\psi_{OF}|^2=|\psi_R|^2+|\psi_{OF}|^2+\psi^*_R\psi_{OF}+\psi_R\psi^*_{OF},$$

where $\Psi_R$ and $\Psi_{OF}$ are the reference wave and objective wave. A spatial Fourier Transform was performed on each raw image to reconstruct the digital hologram:

$$FT(I_H)=FT(|\psi_R|^2+|\psi_{OF}|^2)+FT(\psi^*_R\psi_{OF})+FT(\psi_R\psi^*_{OF})$$

The first two terms represent the DC part (zero-order image) of the hologram. $FT(\Psi_R^*\Psi_{OF})$ and $FT(\Psi_R\Psi_{OF}^*)$ are the holographic image and the conjugate image. To obtain a good signal-noise ratio, the zero-order is removed by subtracting the non-zero-path matched image from the raw data. The holographic image part is chosen for further analysis.

Results and Analysis

Motility Contrast Imaging (MCI) was used to generate a two-dimension motility map at a fixed depth in the living tissue (pig oocyte) and to generate a volumetric motility map from a punctuated fly-through. Temporal contrast is calculated as the normalized standard deviation (NSD) at each pixel given by the expression:

$$NSD = MC(x, y, z) = \sqrt{\frac{1}{N}\sum_{t_0}(I(x,y,z;t_0) - \langle I(x,y,z;t)\rangle)^2} \bigg/ \langle I(x,y,z;t)\rangle$$

where $I(x,y,z;t_0)$ is the intensity value of an individual pixel (x,y) of the holographic reconstructed image at time $t_0$ and at depth z. The depth z is fixed in a 2-D motility map. High NSD values mean high temporal fluctuations indicating a high motility, while low NSD values mean low motility.

Figure 3:
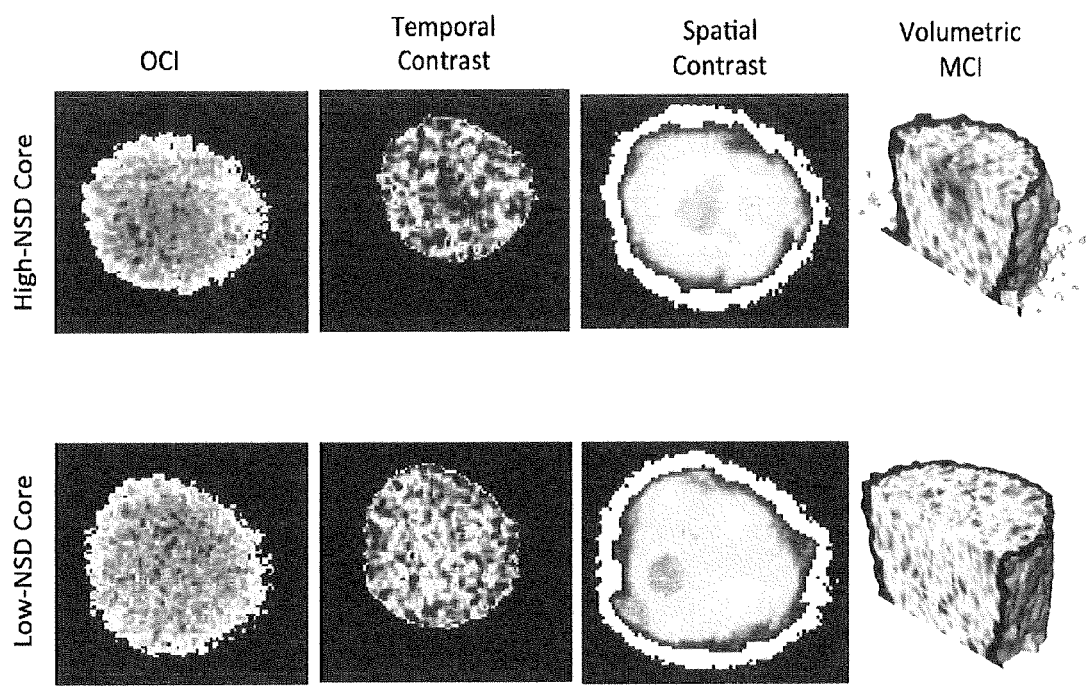
FIG. 3 is a series of motility maps of cumulus-oocyte complexes examined using the system and methods disclosed herein.

Examples of the motility maps of two COCs are shown in FIG. 3, one with a high NSD core and the other with a low NSD core. Both are immature oocytes surrounded by cumulous granulosa cells. The diameter of the cellular structure is approximately 300 μm and the diameter of the central oocyte is approximately 100 μm. Color can be used to indicate the NSD value, with blue denoting low motility and red denoting high motility. Optical coherence imaging (OCI) and motility contrast imaging (MCI) are speckle-based imaging techniques that use speckle contrast to measure physiological properties of live tissue. Temporal contrast from MCI provides a measure of dynamic physiology, while spatial contrast from OCI provides a measure of structure and morphology.

FIG. 3 shows three mid-sections of the holographic data for the same two immature cumulus-oocyte complexes. The mid-section images on the left are the optical-coherence images (OCI), which are the reconstructed holograms of the samples. The grayscale is logarithmic, where a darker gray denotes high reflectance, and a lighter gray denotes low reflectance. The middle images are the temporal contrast (NSD) on a linear grayscale with dark denoting high temporal fluctuations and light low fluctuations. The mid-section images on the right are the spatial contrast on a linear scale with darker denoting low spatial contrast and lighter high spatial contrast.

The COC in the upper panels of FIG. 3 shows stronger motion in the oocyte than the surrounding cumulous cells, indicating a "good" oocyte. On the other hand, the oocyte in the bottom panels of the figure shows an even weaker motion than the surrounding cumulous cells, denoting a "bad" oocyte. As the images demonstrate, there is a correlation between the temporal NSD map and spatial NSD map. In particular, the oocyte in the upper panels with a high temporal NSD core area has a corresponding low spatial NSD core area. The oocyte in the lower panels of FIG. 3 without a low temporal NSD core area has no corresponding low spatial NSD core area. The volumetric motility maps of the oocytes reflect the same activity/inactivity patterns.

The OCI results show no discernible oocyte within the cumulus investment. This is believed to be because the relatively long coherence of the light source (30 microns) and the low spatial resolution (also 30 microns) produces high-contrast speckle with little structural content. However, the same highly-developed speckle provides high temporal contrast that shows a strong activity in the core in the one COC but not in the other. The spatial contrast shows a trend similar to the temporal contrast. The "active" COC in the upper panels of FIG. 3 has low spatial contrast in the core, but the "inactive" COC has higher spatial contrast.

To one versed in the art, the application of MCI to COCs would not have been expected to yield the positive results shown in FIG. 3. All previous applications of MCI were on multi-cellular samples that have many cells per imaging volume. Cellular membranes are sources of scattered light, which makes multi-cellular tissue samples bright in back-scattered light. The oocyte, on the other hand, is a single large cell with a diameter of ~100 microns. There are many volume elements contained within the oocyte volume, and hence the internal volume of the oocyte would not be expected to be bright enough to detect using MCI. The internal structure and motions of the oocyte generate a detectable MCI signal in spite of the lack of extracellular membranes. It is apparent that high density of mitochondria and internal membranes of the oocyte make up the source of the MCI signal. Therefore, MCI is shown here for the first time to be extended into the single-cell regime, specifically for the application to oocyte viability assessment.

Figure 4:
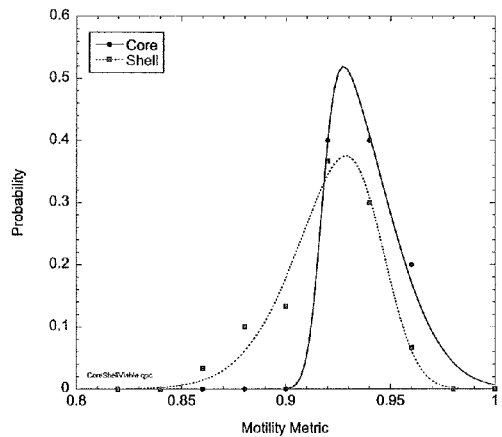
FIG. 4 is a histogram of the shell motility metric compared to a histogram of the core motility metric.
Figure 5:
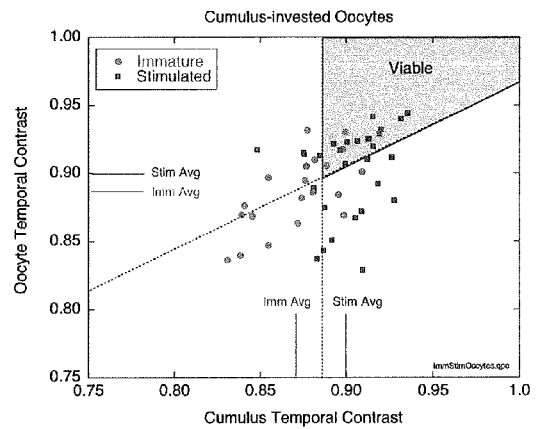
FIG. 5 is a graph correlating the core motility metric with the shell motility metric for many COCs including the COCs shown in FIG. 2.

It is demonstrated that the healthy oocytes have higher cellular motion than the surrounding cumulus cells on average. Histograms of the motility of the shell and the core (oocyte) are shown in FIG. 4. The NSD values (calculated according to the equation above) of oocyte (core area) plotted against the average NSD values of the cumulus cumulus cells (shell area) are shown in the temporal contrast graph of FIG. 5. The circle data points are oocytes which were observed in their immature state, while the square data points are oocytes which were observed after they were matured in vitro in the presence of follicle stimulating hormone (FSH) and luteinizing hormone (LH). Data points above the diagonal line correspond to stronger motion in the oocyte than in the cumulus investment. The average NSD value for the matured oocytes is shifted to the right from the average value for the immature oocytes, indicating that maturation in the presence of FSH and LH increases the average sub-cellular motion of both the cumulus and the oocyte.

Figure 6:
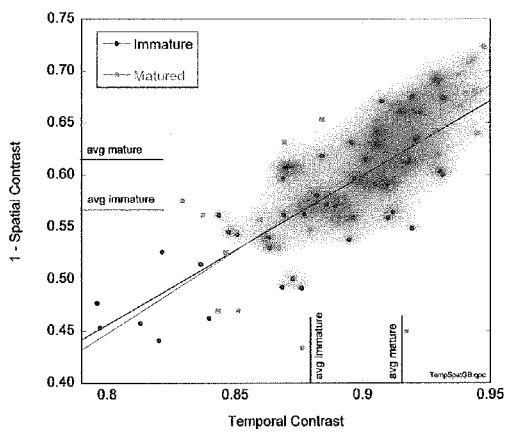
FIG. 6 is graph correlating the temporal and spatial contrasts for the oocytes shown in FIG. 7 shows histograms of a viability metric for matured and immature COCs according to the systems and methods disclosed herein.

The correlation of the spatial contrast of OCI with the temporal contrast of MCI is shown in FIG. 6 for the immature and in vitro matured oocytes. The correlation coefficient from the linear fit is 0.80 for the immature oocytes and 0.73 for the matured oocytes. It is important to note that while the nucleus is usually in the center of the oocyte for viable oocytes, some non-viable oocytes have asymmetric nucleus location and are believed to have higher cytoplasmic heterogeneity which may explain the strong correlation between high temporal and low spatial contrast, both of which can be indicative of a viable oocyte for fertilization. As the graph of FIG. 6 illustrates, the increase in average temporal contrast from immature to maturation is greater than the increase in average spatial contrast from immature to maturation. In addition, as reflected in the graph of FIG. 4, the average increase in temporal contrast of the cumulus shells upon maturation is larger than the increase in temporal contrast values for the oocytes. The shaded triangle in the upper right of FIG. 4 denotes the oocytes that have high activity and that respond to hormonal stimulation. Viable oocytes that are ready for IVF would be selected from this region.

Figure 7:
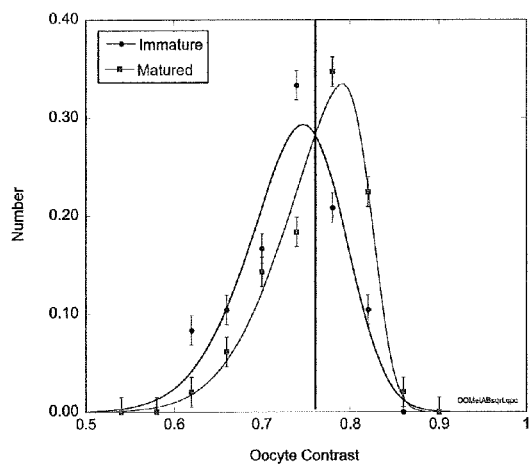

These data suggest a "viability" figure of merit $V = \sqrt{T(1-S)}$, where T is the temporal contrast value and S is the spatial contrast value. Histograms of this figure of merit are shown in FIG. 7 for immature (circles) and in vitro matured COCs (squares), with the x-axis corresponding to the V value and the y-axis corresponding to the number of oocytes. The skewed peak in the matured histogram may be a potential indicator of oocyte viability for subsequent fertilization. For the present example, the "viability" line in FIG. 7 corresponds to the intersection of the two histograms with oocytes having a V value to the right of this line deemed to be viable.

Figure 8:
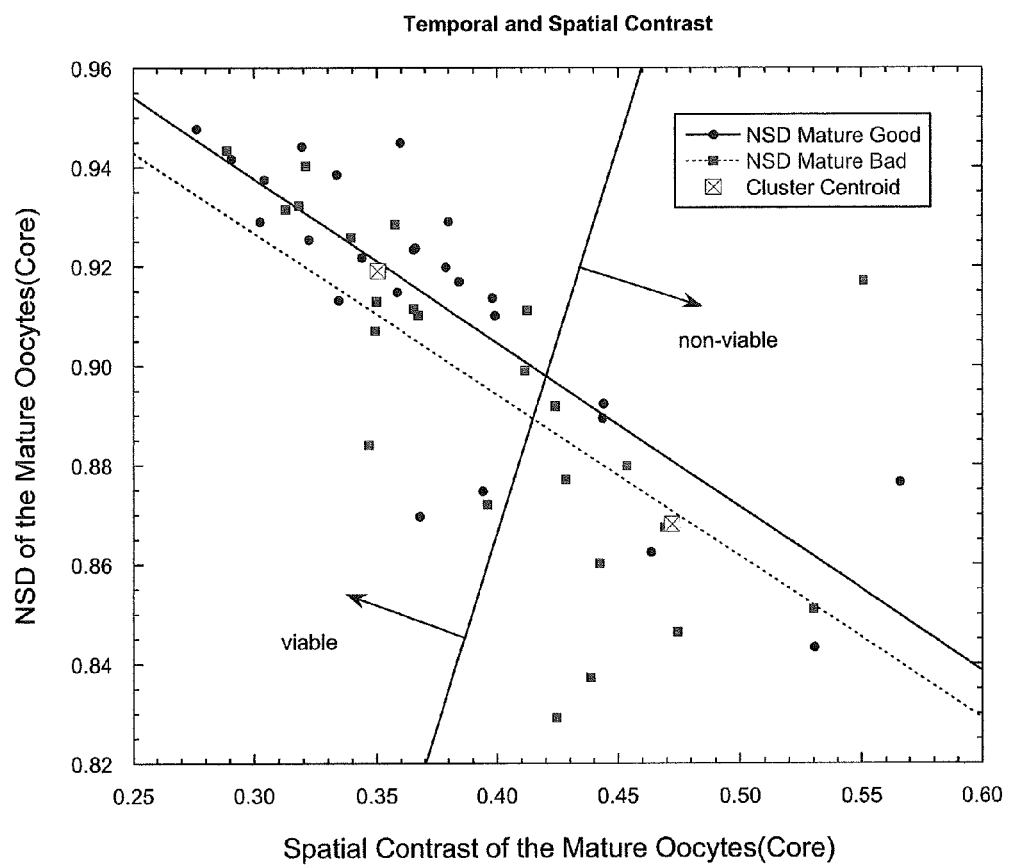
FIG. 8 is graph correlating the motility metric (NSD) of mature oocytes to the spatial contrast of the same oocytes.

FIG. 8 presents a graph in which the x axis is the spatial contrast value of the core area of the mature oocytes and the y axis is the NSD (temporal) value of the same oocytes. Circle data points are the oocytes marked "good" by the technician, while the square points are the oocytes marked "bad". The graph illustrates that the oocytes with low spatial contrast values tend to have high NSD values indicative of an active and healthy oocyte. Conversely, oocytes with high spatial contrast tend to have lower NSD values, indicative of an inactive or unhealthy oocyte. K-means clustering can be applied to the data to reveal two clusters divided between the centroids of the clusters by the line in the graph. One cluster to the left of the line is the low spatial contrast, high NSD group. Points in this cluster are dense and close to each other. The other cluster to the right of the line is the high spatial contrast, low NSD group. Points in this group distribute wider than the other cluster. Note that for the "good" oocytes group, 80% of the oocytes are in the low spatial contrast, high NSD cluster, while for the "bad" group, the oocytes nearly equally distribute between the two clusters (58%:42%).

Figure 9:
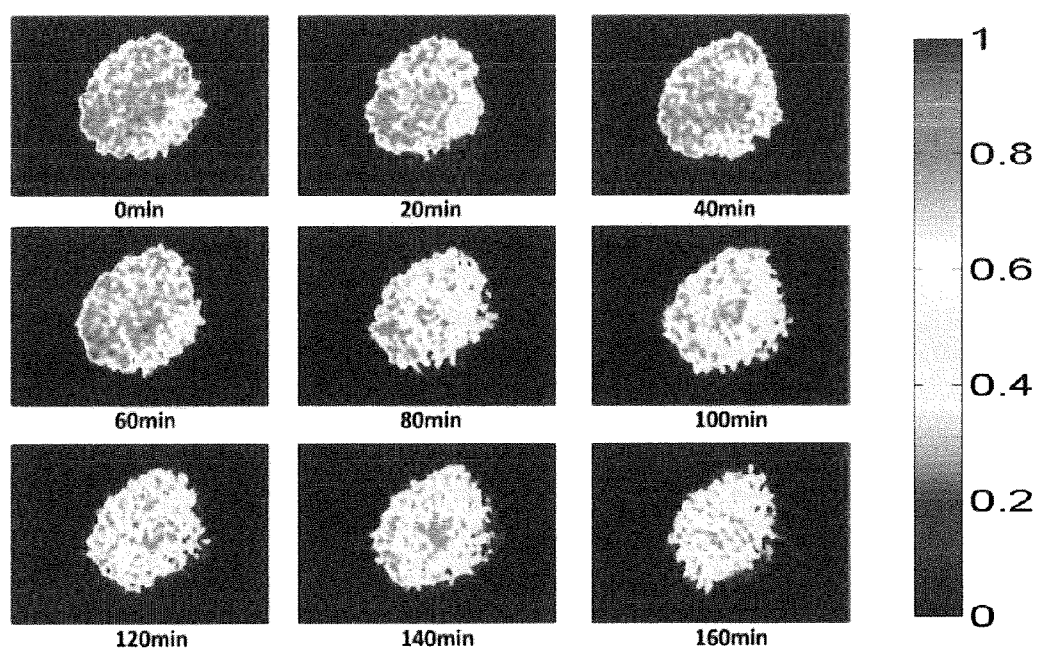
FIG. 9 is a motility map of an immature granulosa-encased oocyte as a function of temperature decreasing over time.

Temperature is an important factor for the oocyte health. As demonstrated in the images of FIG. 9, when the temperature decreased from the pig physiological temperature (39° C.) at time 0, to room temperature (25° C.) at time 160 min., the motility of the cumulus-encased oocyte decreased over time until it was relatively inert.

Figure 10:
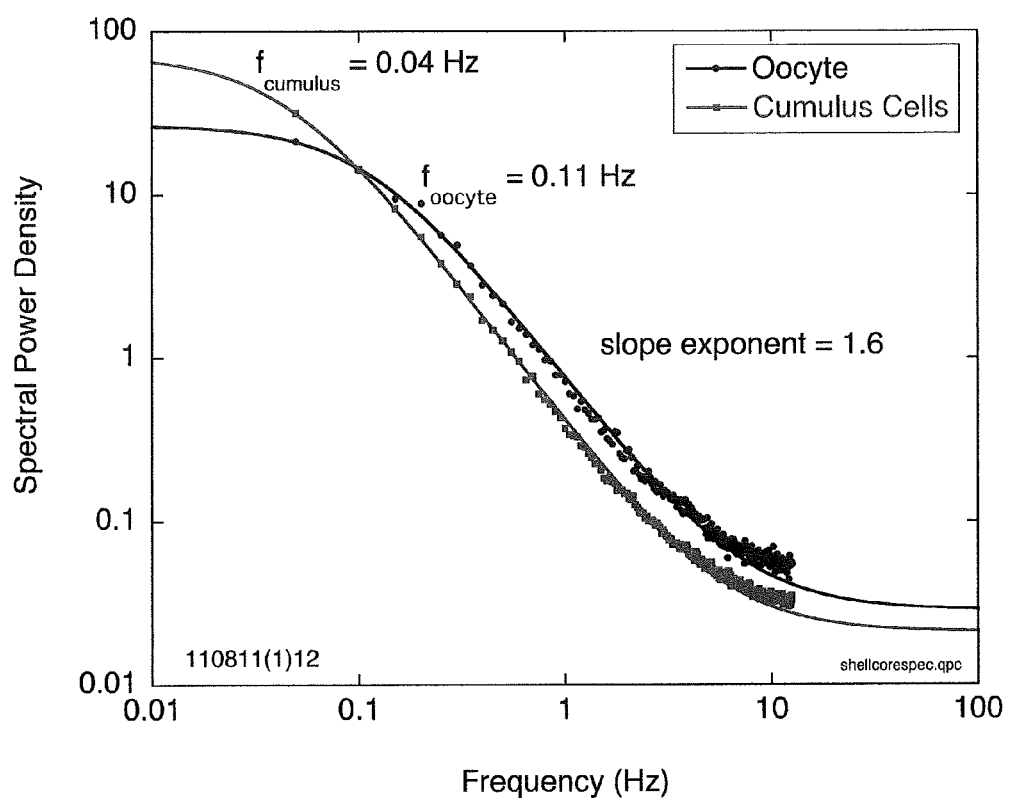
FIG. 10 is a spectral density graph comparing an active oocyte to the cumulus shell.

The power spectra of a cumulus shell and an oocyte are shown in FIG. 10. There are characteristic differences in the knee frequencies and in the frequency content. In particular, in this quantitative comparison the oocyte power spectrum has a higher knee frequency at about 0.11 Hz than the cumulus cell knee frequency of about 0.04 Hz. The slope exponent for both oocyte and cumulus cells is about 1.6.

Figure 11:
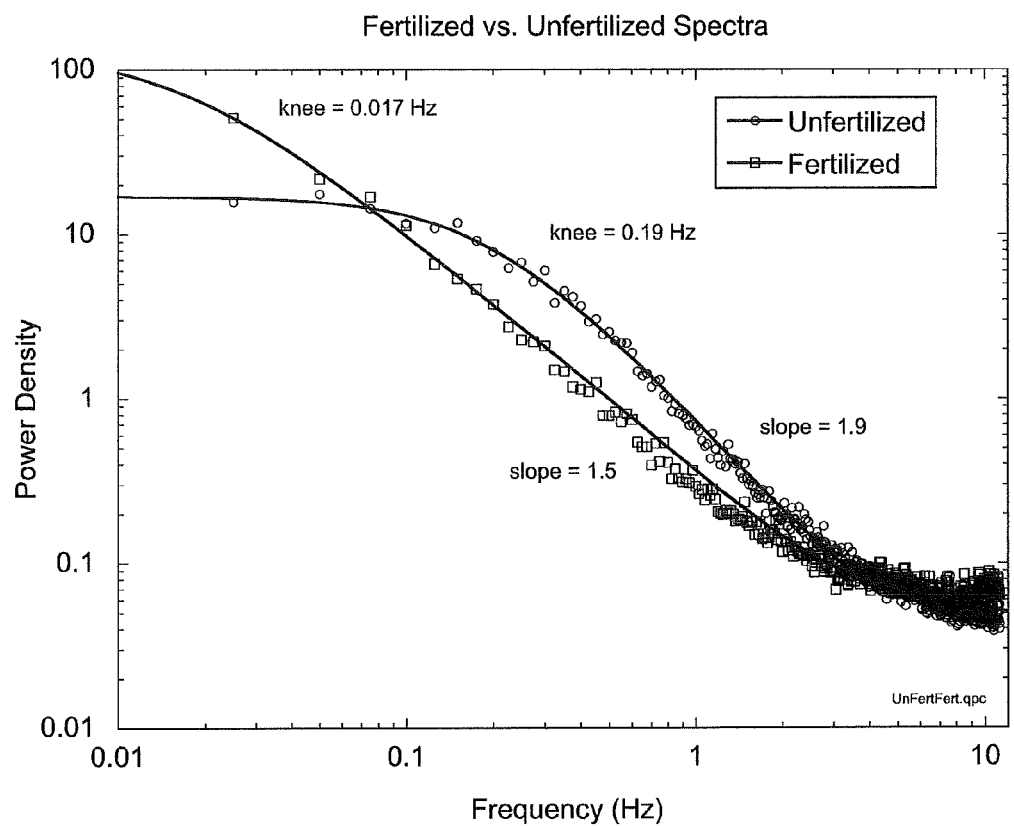
FIG. 11 is a spectral density graph comparing a fertilized oocyte to an unfertilized oocyte.

A key step in the IVF process is fertilization of the oocyte to form a zygote that develops into a blastocyst. The fertilization step has many failure modes, and approximately only 50% of porcine oocytes become correctly fertilized. For subsequent selection for implantation, assessment of the fertilized zygote is valuable. A dramatic shift in the power spectrum of a freshly-formed zygote relative to an unfertilized oocyte is shown in FIG. 11, which is, unexpected to one trained in the art. The unfertilized oocyte has a higher knee frequency than the fresh zygote. The process of zygote formation suppresses overall motion, with an enhancement in low frequencies. In addition the slope exponent decreases from 1.9 to 1.5 representing the onset of "anomalous" transport inside the zygote. The fluctuation spectra provide an accurate set of metrics to distinguish fertilized from unfertilized specimens.

In accordance with the present invention, analysis of experimental physical properties of the zygotes as well as quantitative metric values obtained from the fluctuation power spectrum provide a new approach to selecting fertilized oocytes. To demonstrate this approach, the oocyte data used for principal component analysis (PCA) contain two cohorts: one with 35 unfertilized oocytes and the other with 51 nominally fertilized oocytes. It must be understood that the unfertilized oocytes are all unfertilized, but while the fertilized oocytes have been exposed to sperm they may not have been correctly fertilized. For instance, the normal successful fertilization rate is less than 50%. Furthermore, the health of each fertilized oocytes is different from each other. Therefore, the goal is to select the best fertilized oocyte to pass through to the following steps in IVF.

After calculating the principal components for both unfertilized and fertilized oocytes, PCA is performed for all the oocytes. The principal components are shown in Table. 1. It shows that the backscatter brightness, the spatial contrast and the slope of spectrum are the main contributors to the components. The total contribution for these three is 63.5%.

TABLE 1

Principal components and their weight from the PCA analysis

| | Principal Component | Weight |
|---|---|---|
| 1 | Backscatter brightness | 24.2% |
| 2 | Spatial contrast | 22.3% |
| 3 | Slope of spectrum | 17.0% |
| 4 | Knee frequency of spectrum | 13.3% |
| 5 | Power intensity of the very lowest frequency point | 10.8% |
| 6 | Ellipticity | 7.3% |
| 7 | Temporal contrast | 5.1% |

Figure 12:
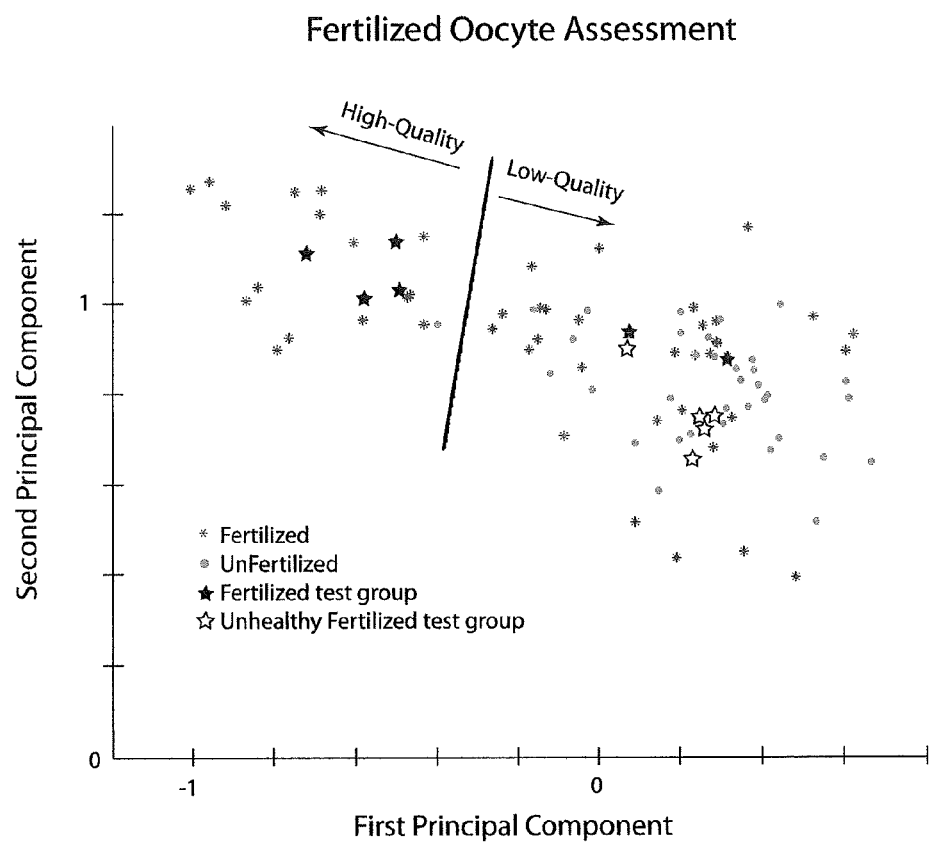
FIG. 12 is a principal-component analysis plot of oocytes in fertilized and unfertilized groups.

A two-dimensional PCA map is shown in FIG. 12. The circles represent the unfertilized oocyte group and the asterisks represent the fertilized oocyte group. The circles are close to each other and cluster together, and the PCA map demonstrates the common character of the unfertilized oocytes. However, the asterisks are distributed over the entire space. About ⅔ of the asterisks overlap with the circles and another ⅓ are well-separated from the others. Therefore, this distribution demonstrates that ⅔ of the oocytes in the fertilized oocyte group have the same character as the unfertilized group. This result suggests that these two-thirds of the so-called fertilized oocytes in fact had not successfully been fertilized. This important step shows that biodynamic spectroscopy can recognize unfertilized oocytes and pick the healthy candidates among fertilized oocytes.

To further validate this approach, two groups of oocytes were processed as test groups. One group was a set of healthy oocytes that followed the normal fertilization process, designated by filled stars in FIG. 12. The other group, designated by open stars, consisted of unhealthy oocytes (treated with low temperature before experiment). In FIG. 12, six normal fertilized oocytes (filled stars) and five unhealthy fertilized oocytes (open stars) are plotted on the 2D PCA map. Although all the open stars are in the unfertilized zone, the healthy fertilized oocytes are split into both zones. This primary validation shows the robustness of the biodynamic imaging technology.

Figure 13:
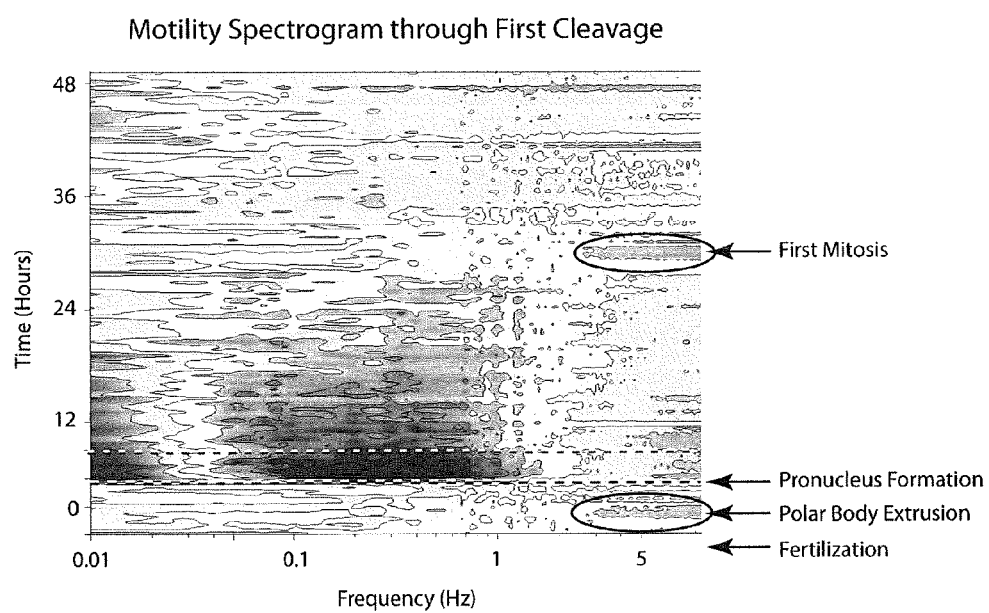
FIG. 13 is a spectrogram of a zygote that undergoes mitosis.

Spectrogram analysis is a powerful tool in biodynamic imaging technology because it traces different kinds of cellular motion as spectral fingerprints. FIG. 13 shows a biodynamic image that has captured the mitotic spectral fingerprint of a fertilized oocyte. The spectrogram in FIG. 13 shows a strong mid frequency enhancement that begins about 4 hours after fertilization and is sustained over the first 24 hours. This time period is consistent with pronucleus formation which occurs prior to mitosis. After 24 hours, the enhancement shifts briefly to the high frequency range, denoting a short term of high activity (cytokinesis), after which it shifts to the low-frequency range.

Figure 14:
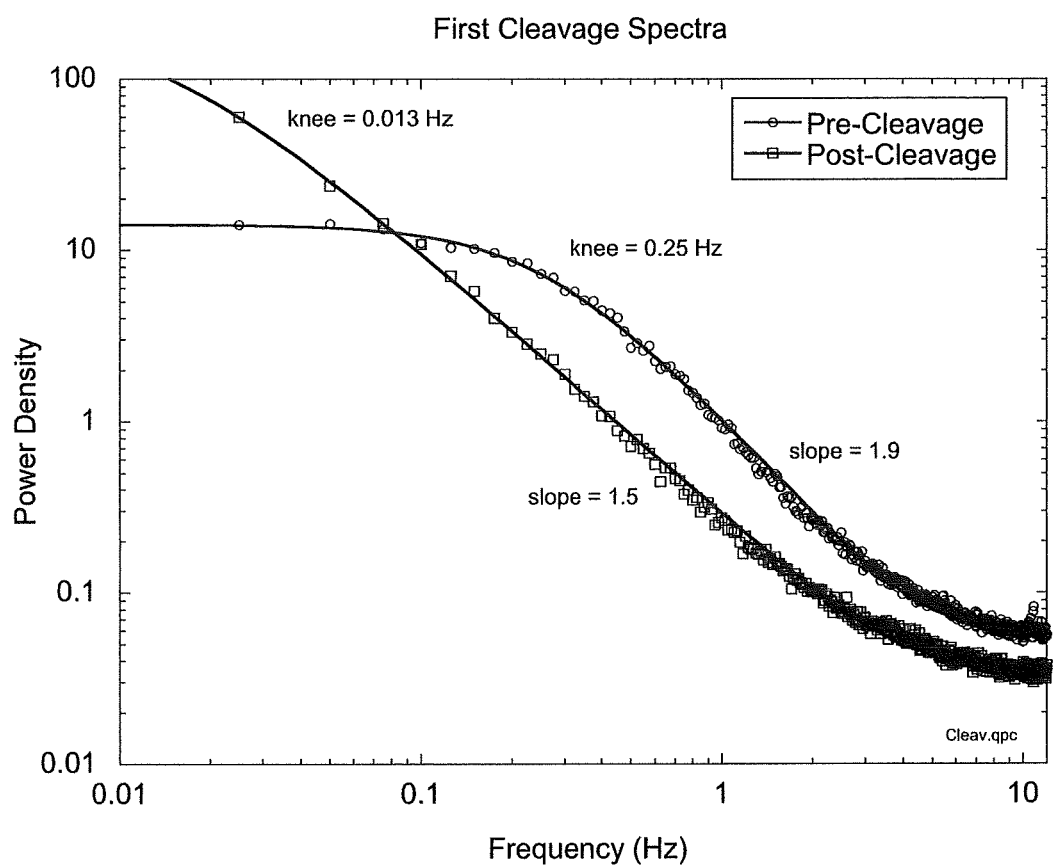
FIG. 14 is a spectral density graph of the zygote before, during and after mitosis.

It is important to note that the OCI image of the dividing zygote had limited spatial resolution and hence did not show strong evidence for division. However, from the spectrogram, the mitotic event occurred after 24 hours. The power spectra in FIG. 14 show the spectral difference before and after mitosis. The zygote shows strong and rapid motions leading up to mitosis, but immediately after cytokinesis the motions become much more quiescent. The spectrogram contains high information content which pertains to the specific physical processes involved in the first cleavage and can be used as metrics or indicators of the potential of the sample for implantation.

Embodiments

In vitro fertilization success relies on accurate assessment of oocyte viability after harvesting, during maturation, and after fertilization. Oocytes invested with cumulus granulosa cells, called cumulus-oocyte complexes (COCs), are not readily visible under a microscope, making viability grading difficult. As described herein, one embodiment of the present invention contemplates using motility contrast imaging (MCI) to measure oocyte activity before and after maturation induced by follicle stimulating hormone (FSH). MCI uses digital holography [14-17] as the coherence gate for low-coherence interferometry [18-20] to capture dynamic light scattering from intracellular motions. High temporal contrast of the fluctuating speckle is correlated with low spatial speckle contrast in the optical coherence imaging data. Using these tools, the changes in intracellular activity induced by FSH, and the differences in the fluctuation spectra between the cumulus shell and the oocyte, can be evaluated to provide potential new biomarkers for assisted reproductive technology.

Using the system and method described herein, assessing reproductive cells, such as oocytes and embryos can be made routine and can simplify the candidate selection process. In a "Domestic Animal IVF Laboratory" hundreds of oocytes are available after collection so it is easier and more economical to simply discard oocytes that have no chance to form viable embryos. However, in a "Human IVF Laboratory" the number of oocytes collected from a woman is usually limited, maybe only up to 20 oocytes. The evaluation of viable cells thus becomes much more critical. In one aspect, assessing oocyte viability and quality can improve the human IVF process. Going further, assessing embryo viability and quality can be particularly valuable to determine whether a particular embryo has the potential to develop to term. Traditional methods, such as morphological assessment, are not reliable because an embryo can look good under a microscope yet have low developmental potential. For this purpose it is first important to use good quality oocytes and then fertilize them to generate embryos. The embryos may then be evaluated using the same biodynamic imaging techniques described herein to select the "good" embryos with the highest likelihood of developing to term.

In one aspect of the present invention, Motility Contrast Imaging (MCI) is applied to measure the dynamic activity of cumulus-invested oocytes (including immature oocytes and oocytes matured in vitro) which are not readily visible under a microscope. The physiological characteristics of the oocytes are measured non-invasively by using motion as an endogenous imaging contrast agent. MCI has interferometric sensitivity to cellular displacements of a fraction of a wavelength by treating each speckle as an independent interferometer. The ability to measure sub-micron displacements over a field of view of a millimeter represents a large dynamic range that could prove useful for key indicators for reproductive cell viability applications, including assessing viability of oocytes and embryos.

In one embodiment, the present invention provides a method for evaluating viability of oocytes and embryos comprising imaging oocytes and embryos using MCI; generating temporal contrast and spatial contrast data for the cells; generating a cell viability value as a function of the temporal and spatial contrast data; and comparing the cell viability value to a predetermined value indicative of a cell suitable for use in an in vitro fertilization program.

In a further embodiment, the fluctuating light intensities from the speckle images are analyzed by their frequency content and how they change as a function of time. This method is called tissue dynamics spectroscopy (TDS). From the analysis, the system measures the low, mid and high frequency fluctuation spectral content changes over the time development of the reproductive specimen (e.g., oocytes, and embryos up to the blastocysts stage). The resulting dynamic spectroscopy provides a matrix of measurement values that are related to the health and viability of the specimen.

A system is envisioned that combines MCI and TDS in a single measurement system. This system provides quantitative measures of specimen health and potential reproductive viability, as well as time-evolving dynamics and dynamic maps that would show heterogeneous properties of the reproductive specimen.

According to one method, the system performs statistical analysis on the spectral content to generate spectrogram fingerprints averaged over specified areas (volumes) of the reproductive specimen. A library of these fingerprints can be assembled that are cross-correlated with known pathologies of reproductive specimens. In the present method, a specimen will be measured and analyzed into a spectrogram fingerprint that is compared to the reference library. In this manner, a specimen will be graded as "viable" or "pathological" depending on the comparison to the spectrogram library. Decisions to select or reject this reproductive specimen may be made based on this comparison.

While the invention has been illustrated and described in detail in the drawings and foregoing description, the same should be considered as illustrative and not restrictive in character. It is understood that only the preferred embodiments have been presented and that all changes, modifications and further applications that come within the spirit of the invention are desired to be protected.

REFERENCES

[1] T. Ebner, M. Moser, M. Sommergruber, and G. Tews, "Selection based on morphological assessment of oocytes and embryos at different stages of preimplantation development: a review," Human Reproduction Update, vol. 9, pp. 251-262, May-June 2003.
[2] C. Sato, M. Shimada, T. Mori, Y. Kumasako, E. Otsu, H. Watanabe, and T. Utsunomiya, "Assessment of human oocyte developmental competence by cumulus cell morphology and circulating hormone profile," Reproductive Biomedicine Online, vol. 14, pp. 49-56, January 2007.
[3] M. Salvador, J. Prauzner, S. Kober, K. Meerholz, K. Jeong, and D. D. Nolte, "Depth-resolved holographic optical coherence imaging using a high-sensitivity photorefractive polymer device," Applied Physics Letters, vol. 93, Dec. 8, 2008.
[4] K. Jeong, J. J. Turek, and D. D. Nolte, "Fourier-Domain Digital Holographic Optical Coherence Imaging of Living Tissue," Appl. Opt., vol. 46, pp. 4999-5008, 2007.
[5] K. Jeong, L. Peng, J. J. Turek, M. R. Melloch, and D. D. Nolte, "Fourier-domain holographic optical coherence imaging of tumor spheroids and mouse eye," Appl Opt, vol. 44, pp. 1798-805, Apr. 1, 2005.
[6] D. D. Nolte, R. An, K. Jeong, and J. Turek, "Holographic Motility Contrast Imaging of Live Tissues," Chap. in Biomedical Optical Phase Microscopy and Nanoscopy, N. T. Shaked, Z. Zalevskey, and L. Satterwhite, Eds., ed: Elsevier, 2012.
[7] D. D. Nolte, "Dynamic Light Scattering and Motility Contrast Imaging in Living Tissue," Chap. in Biomedical Applications of Light Scattering, A. Wax and V. Backman, Eds., ed: McGraw Hill, 2010.
[8] K. Jeong, D. D. Nolte, J. J. Turek, and Ieee, Phase-Sensitive Motility Contrast Imaging of Tumor Response to Drugs, 2010.
[9] D. D. Nolte, R. An, J. J. Turek, and K. Jeong, "Tissue dynamics spectroscopy for phenotypic profiling of drug effects in three-dimensional culture," Biomed. Opt. Express, vol. 3, pp. 2825-2841, 2012.
[10] D. D. Nolte, R. An, J. Turek, and K. Jeong, "Holographic tissue dynamics spectroscopy," Journal of Biomedical Optics, vol. 16, pp. 087004-13, August 2011.
[11] D. D. Nolte, R. An, J. Turek, and K. Jeong, "Tissue Dynamics Spectroscopy for Three-Dimensional Tissue-Based Drug Screening," Jala, vol. 16, pp. 431-442, December 2011.
[12] K. Jeong, J. J. Turek, and D. D. Nolte, "Imaging Motility Contrast in Digital Holography of Tissue Response to Cytoskeletal Anti-cancer Drugs," Optics Express, vol. 15, pp. 14057-14064, 2007.
[13] K. Jeong, J. J. Turek, M. R. Melloch, and D. D. Nolte, "Multiple-scattering speckle in holographic optical coherence imaging," Applied Physics B-Lasers And Optics, vol. 95, pp. 617-625, June 2009.
[14] I. Yamaguchi and T. Zhang, "Phase-shifting digital holography," Optics Letters, vol. 22, pp. 1268-1270, Aug. 15, 1997.
[15] E. Cuche, F. Bevilacqua, and C. Depeursinge, "Digital holography for quantitative phase-contrast imaging," Optics Letters, vol. 24, pp. 291-293, Mar. 1, 1999.
[16] F. Dubois, L. Joannes, and J. C. Legros, "Improved three-dimensional imaging with a digital holography microscope with a source of partial spatial coherence," Applied Optics, vol. 38, pp. 7085-7094, Dec. 1, 1999.
[17] T. S. Huang, "Digital Holography," Proceedings of the Institute of Electrical and Electronics Engineers, vol. 59, pp. 1335-&, 1971.
[18] J. W. Pyhtila, R. N. Graf, and A. Wax, "Determining nuclear morphology using an improved angle-resolved low coherence interferometry system," Optics Express, vol. 11, pp. 3473-3484, Dec. 15, 2003.
[19] G. Popescu and A. Dogariu, "Scattering of low coherence radiation and applications," European Physical Journal-Applied Physics, vol. 32, pp. 73-93, November 2005.
[20] K. J. Chalut, S. Chen, J. D. Finan, M. G. Giacomelli, F. Guilak, K. W. Leong, and A. Wax, "Label-free, high-throughput measurements of dynamic changes in cell nuclei using angle-resolved low coherence interferometry," Biophysical Journal, vol. 94, pp. 4948-4956, Jun. 15, 2008.

What is claimed is:

1. A method for evaluating oocytes and embryos comprising:
   reversibly immobilizing cells by adhering the cells to a surface wherein the cells are oocytes or embryos;
   detecting intracellular motion at a fixed depth within the immobilized cells with a holographic detection system;
   generating cell viability values of the cells based on the detected intracellular motion;
   comparing the cell viability values to a threshold indicative of suitability for use in an in vitro fertilization procedure; and
   selectively removing cells from the surface for implantation wherein the selection of the cells is based upon the cell viability values of the selected cells.

2. The method of claim 1, wherein the step of detecting intracellular motion is performed using motility contrast imaging.

3. The method of claim 1, wherein the step of generating a cell viability value includes determining frequency content of speckle imaging of the cell.

4. The method of claim 3, wherein the step of generating a cell viability value further includes determining the temporal variation of the frequency content of speckle imaging of the cell.

5. The method of claim 3, wherein the step of generating a cell viability value further includes determining the spatial variation of the frequency content of speckle imaging of the cell.

6. The method of claim 5, wherein:
   the step of generating a cell viability value includes:
   determining the temporal variation of the frequency content of speckle imaging of the cell; and
   deriving the cell viability value as a function of the temporal and spatial variation of the frequency content.

7. The method of claim 2, wherein:
   the step of detecting intracellular motion at a fixed depth includes detecting intracellular motion at a plurality of depths within the immobilized cells with a holographic detection system;
   wherein the motility contrast imaging generates a two-dimensional motility map at the fixed depth within the cell and a volumetric motility map to construct a holographic motility image of the cell; and
   the step of generating a cell viability value includes determining the temporal variation of the frequency content of speckle imaging of the cell in which the temporal contrast is determined as a normalized standard deviation of the temporal variation of the intensity of all pixels of the holographic image at a predetermined depth within the cell.

8. The method of claim 1 further comprising changing a condition of the cell and detecting intracellular motion of the cell during the changing condition.

9. The method of claim 8, wherein the changing condition includes one or more of introducing follicle stimulating hormone to the cell and changing the temperature of the cell.

10. The method of claim 1, wherein the step of detecting intracellular motion is performed using tissue dynamics spectroscopy to measure low, mid and high frequency spectral content changes over time and/or to measure the dynamic fluctuation spectrum of selected groups of spatially located pixels.

11. The method of claim 1, wherein the step of detecting intracellular motion is performed by the combined use of motility contrast imaging to measure the temporal and spatial variation of the frequency content of speckle imaging of the cell, tissue dynamics spectroscopy to measure frequency spectral content changes over time, and tissue dynamics spectroscopy to measure low, mid and high frequency spectral content changes over time.

12. The method of claim 11, further comprising generating a spectrogram fingerprint of the cell complex averaged over predetermined portions of the volume of the cell complex.

13. The method of claim 12 further comprising the step of comparing the spectrogram fingerprint of the cell to a reference library of fingerprints indicative of grades of viability.

14. A method for evaluating oocytes and embryos comprising:
   reversibly immobilizing an oocyte or embryo by adhering the oocyte or embryo to a surface in a sample plate;
   placing the sample plate in a fixed mount;
   moving a holographic detection system with negligible vibration relative to the sample plate to detect intracellular motion of the oocyte or embryo;
   generating a cell viability value based on the detected intracellular motion; and
   comparing the cell viability value to a threshold indicative of suitability for use in an in vitro fertilization procedure; and
   when the cell viability value of the oocyte or embryo indicates that the oocyte or embryo is viable, removing the oocyte or embryo from the surface for implantation.

15. The method of claim 14, wherein the holographic detection system is a motility contrast imaging system.

16. A method for evaluating an oocyte comprising:
   reversibly immobilizing a fertilized oocyte by adhering the oocyte to a surface;
   detecting intracellular motion within the immobilized oocyte with a holographic detection system by moving the holographic detection system and the surface to which the oocyte is adhered relative to each other and using motility contrast imaging;
   generating a cell viability value of the oocyte based on the detected intracellular motion; and
   comparing the cell viability value to a threshold indicative of suitability for use in an in vitro fertilization procedure; and
   when the cell viability value of the oocyte indicates that the oocyte is viable, removing the oocyte from the surface for implantation.

17. The method of claim 16 in which detecting intracellular motion within the immobilized oocyte includes evaluation of at least one of the metrics including backscatter brightness, spatial contrast, slope of spectrum, knee frequency, power intensity at low frequency, ellipticity and temporal contrast.

18. The method of claim 17 in which a plurality of the metrics are combined in a principal component analysis to generate the cell viability value.

19. The method of claim 18 in which the principal component analysis is performed on the oocyte cell sample of interest and compared with a set of reference samples to aid evaluation of the viability of the sample.

20. The method of claim 16 in which the duration and magnitude of oocyte activity prior to cleavage is compared with values from reference samples of known viability to evaluate the reproductive potential of the sample.

21. The method of claim 1 in which the step of detecting intracellular motion includes evaluation of at least one of the metrics including backscatter brightness, spatial contrast, slope of spectrum, knee frequency, power intensity at low frequency, ellipticity and temporal contrast.

22. The method of claim 21 in which a plurality of the metrics are combined in a principle component analysis to generate the cell viability value.

23. The method of claim 14 wherein the cell viability value is a function of at least one of the metrics including backscatter brightness, spatial contrast, slope of spectrum, knee frequency, power intensity at low frequency, ellipticity and temporal contrast.

24. The method of claim 23 in which a plurality of the metrics are combined in a principle component analysis to generate the cell viability value.

\* \* \* \* \*